United States Patent [19]

Dryden

[11] Patent Number: 5,269,756
[45] Date of Patent: Dec. 14, 1993

[54] IRRIGATION APPARATUS AND METHOD FOR SUCTION CATHETERS

[75] Inventor: Gale E. Dryden, Indianapolis, Ind.

[73] Assignee: MedicPro Inc., Indianapolis, Ind.

[21] Appl. No.: 976,438

[22] Filed: Nov. 13, 1992

[51] Int. Cl.⁵ .................. A61M 31/00; A61M 25/00; A61M 16/08
[52] U.S. Cl. ..................... 604/54; 604/151; 604/171; 604/283; 128/207.16; 128/912
[58] Field of Search ................... 604/30–37, 604/43, 45, 49, 51, 119, 151–153, 54, 171, 172, 181, 257, 262, 264, 266, 283, 403, 902; 128/207.14–207.16, 912

[56] References Cited

U.S. PATENT DOCUMENTS

| | | | |
|---|---|---|---|
| 1,873,160 | 8/1932 | Sturtevant | 128/207.14 X |
| 3,502,069 | 3/1970 | Silverman | 604/151 X |
| 3,991,762 | 11/1976 | Radford . | |
| 4,805,611 | 2/1989 | Hodgkins | 128/207.14 |
| 4,836,199 | 6/1989 | Palmer | 128/207.16 |
| 4,850,350 | 7/1989 | Jackson . | |
| 4,872,579 | 10/1989 | Palmer | 128/205.19 |
| 4,881,542 | 11/1989 | Schmidt et al. . | |
| 5,025,806 | 6/1991 | Palmer et al. | 128/203.12 |
| 5,029,580 | 7/1991 | Radford et al. | 128/207.14 |
| 5,125,893 | 6/1992 | Dryden . | |
| 5,133,345 | 7/1992 | Lambert | 128/202.16 |
| 5,139,018 | 8/1992 | Brodsky et al. | 128/207.14 |

FOREIGN PATENT DOCUMENTS 1176320 8/1964 Fed. Rep. of Germany ................ 128/207.14

Primary Examiner—John D. Yasko
Assistant Examiner—Adam J. Cermak
Attorney, Agent, or Firm—Woodard, Emhardt, Naughton, Moriarty & McNett

[57] ABSTRACT

A cased suctioning catheter assembly with a protective flexible sheath around the catheter tube, has a thumb or finger operable pump located near the patient end of the catheter assembly. This pump receives irrigation fluid from a bag hanging on an IV stand and, when operated, pumps it into an irrigation lumen in the suction catheter on an as-needed basis during suctioning. Thereby one hand of the administrator can both stabilize the cross piece at the patient end of the suction catheter assembly and operate the irrigator, while the other hand controls vacuum flow as needed for the suctioning function.

10 Claims, 1 Drawing Sheet

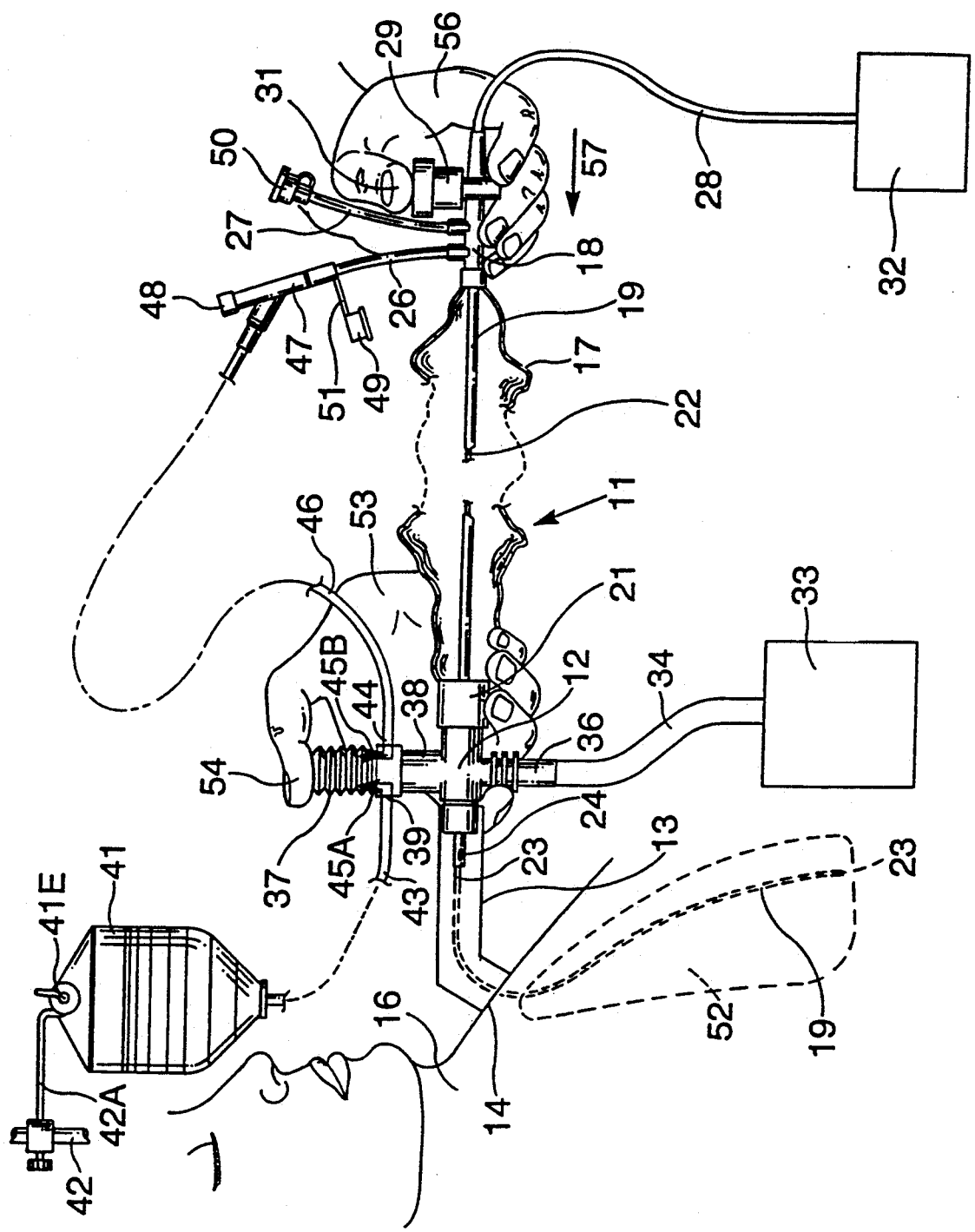

5,269,756

IRRIGATION APPARATUS AND METHOD FOR SUCTION CATHETERS

BACKGROUND OF THE INVENTION

1. Field of the Invention

This invention relates generally to suction catheters, and more particularly to a method and apparatus for keeping them clear so that effective suctioning can be maintained.

2. Description of the Prior Art

In the use of endotracheal tubes, regardless of whether passed through the mouth or through a tracheotomy, there are times when lung secretions are too thick and sticky to be easily extracted through a suction catheter. Dilution helps thin the secretions and irrigate the catheter lumen so good vacuum flow is maintained, thereby promoting removal of lung secretions which must be removed from the lung.

The current practice of irrigation uses syringes or compressable vials as means of instilling the irrigation solution into the lung along the exterior of the catheter or through a lumen inside the wall of the catheter in order to promote dilution. This practice requires more than two hands or the interruption of the suction flow in order to instill the irrigating fluid into the system. A break in the suction flow may cause the secretion pool to be incompletely removed. Also, there is the possibility that the volume of irrigation fluid from the single loaded syringe or vial may not be adequate and will require a reload effort.

SUMMARY OF THE INVENTION

Described briefly, according to a typical embodiment of the present invention, a thumb or finger operable pump is located near the patient end of the suctioning catheter assembly. This pump receives the irrigation fluid from a comparatively large reservoir and can withdraw the fluid from the reservoir and pump it into an irrigation supply channel in the suction catheter on an as-needed basis during suctioning. Thus, the one hand of the administrator can both stabilize the junction piece at the patient end of the suction catheter and operate the irrigator while the other hand controls vacuum flow and catheter location as needed for the suctioning function.

BRIEF DESCRIPTION OF THE DRAWING

The single FIGURE of drawing is a schematic illustration of a cased suction catheter situated for use through a tracheotomy and employing irrigation according to the method and apparatus of the present invention.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawing, a cased suction catheter assembly 11 of the general type shown in my U.S. Pat. No. 5,125,893, issued Jun. 30, 1992, is provided with a four-way junction or cross piece 12 at the patient end (where the tee piece 17, shown in FIG. 1 of that patent, was located in the patent) and to which is connected an endotracheal tube 13 entering the trachea (not shown) through a tracheotomy 14 in the neck 16 of the patient. The flexible sheath 17 is connected and sealed to a sleeve 21 received on the end of the cross piece opposite the endotracheal tube. The distal end of the sheath is connected and sealed to the manifold 18.

A catheter tube 19 is fixed in the manifold 18 but slidably received in the sleeve 21 which may have a valve in it (such as valve 23 shown in FIG. 1 in the above-mentioned patent). The catheter tube 19 has an internal lumen 22 which is like and has the same purpose as the lumen 29 in the catheter tube 20 of the aforementioned patent. The patient end of the catheter tube is open at 23 and the lumen 22 opens in the side of the catheter at the patient end at opening 24 from which irrigation fluid can be discharged into the lung around the catheter.

The lumen 22 communicates with the irrigation fluid supply tube 26 connected to the manifold 18. A suction tube 28 is connected to the manifold 18 and through it to the catheter tube 19. However, this suction line is independent of and isolated from the lumen 22 and associated tube 26. A manually operable vacuum control valve 29 is associated with the vacuum line 28 at the manifold. The valve is normally closed but can be opened by the thumb 31 of the administrator. The line 28 is connected to a suction source 32.

An air/oxygen ventilating machine 33 is connected through hose 34 to the bottom stem 36 of the cross fitting 12. According to the illustrated embodiment of the present invention, a self-priming pump assembly 37 is connected to the top stem 38 of the cross fitting. The intake port 39 of the pump is connected to a comparatively large reservoir such as an IV infusion bag 41 which can be hung on arm 42A of an IV stand 42 by means of the eyelet 41E at the top of the bag. The outlet line 43 of the bag is connected to the inlet port 39 of the pump assembly 37. The discharge port 44 of the pump is connected through the tube 46 to a Y-connector 47 which is, in turn, connected to the tube 26. A needle pierceable cap 48 is provided at the upper end of the other branch of the Y-fitting 47 for addition of material to the irrigation system from a syringe if, and when, desired. An overcap 49 on a flexible hinge 51 is provided on the upper end fitting of tube 26 to close that tube if the Y-connector 47 is removed from it. Similarly, hinged overcap 50 is provided at the upper end of the tube 27.

Two one-way valves shown schematically at 45A and 45B are provided between the inlet and outlet ports 39 and 44 of the pump assembly 37. Thus, irrigating fluid can be drawn from line 43 through valve 45A into the pump bellows, and squeezed out by pressure from the thumb of one hand of the administrator and through the one-way valve 45B into the line 46 and thereby through the tube 26 and lumen 22 and out through the opening 24 when in the patient's lung 52, as indicated by the dotted line in the drawing.

OPERATION

As one hand 53 stabilizes the cross fitting 12 and is in position for operation of the pump with the thumb 54 when irrigation is needed, the catheter tube 19 is pushed down into the lung by advancing the other hand 56 forward in the direction of arrow 57. Suctioning can be increased or decreased by decreasing or increasing the opening in vacuum inlet valve 29 by operating the thumb 31. Irrigation is applied as needed by operating the pump 37 by pushing and releasing the upper end of the bellows with the thumb 54.

The pump, being securely attached to the patient end of the cased suction catheter assembly at the cross piece 12, allows the hand that stabilizes the cross piece to also activate the pump which refills automatically, thus permitting fluid irrigation as long as is needed. The other hand controls the vacuum flow as needed to complete the treatment.

Although the above-described and illustrated pump system lines 46, 26 communicate with an in-the-wall lumen 22 in the catheter, the pump system and line 46 may be connected to line 27 for down-the-catheter lumen purge of the catheter 19 itself in those types of cased catheters which irrigate the interior of the catheter tube itself rather than irrigating at the tip of the catheter. Alternatively or in addition, the irrigation line 46 can be at the patient connector for external wash of the catheter itself. An example would be connection to port 55 of the catheter assembly shown in the U.S. Pat. No. 3,991,762 issued Nov. 16, 1976 to Radford.

If there is any concern about possible confusion between IV lines and bottles with the irrigation system lines and bottles, the apparatus may be sized and/or color coded, and the spike for entering the fluid bag would not have a drip chamber. Similarly, the distal fitting that enters the irrigation sites can be sized or keyed to prevent connection with an intravenous needle or IV lines.

The pump bellows illustrated, or cylinder if a piston pump is used, can be filled from the bag many times by simply releasing thumb pressure from the valve button and without letting go of the catheter system at all. If a piston/cylinder pump is used, the piston pressure of the pump can be changed by the amount of thumb pressure on it. For different situations where nominal thumb pressure might be needed to produce more or less pressure, the amount applied by a given amount of force on the thumb can be determined by selection of appropriate piston diameter. Since it is preferred that the pump be self-priming, the reservoir need not be an elevated bag, but can simply be a bag or other container resting on a surface in the patient area.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Suction catheter apparatus comprising:
   an elongate flexible bag having two ends;
   a first connector fitting coupled to one end of the bag;
   a second connector fitting coupled to the other end of the bag;
   an endotracheal tube coupled to the first connector fitting for introduction to the trachea of a patient to be treated;
   a catheter tube anchored to the second connector fitting and extending through the bag and the first connector fitting into the endotracheal tube; and
   a liquid moving pump mounted to the first connector fitting for connection to a source of irrigation fluid, said pump having an operator member situated adjacent the first connector fitting so as to be operable by a digit of a hand holding the first connector fitting.

2. The apparatus of claim 1 and further comprising:
   a conduit from the pump to a point adjacent the catheter tube to convey irrigation fluid from the pump to contact with the catheter tube.

3. The apparatus of claim 2 and wherein:
   the conduit is coupled to the second connector fitting.

4. The apparatus of claim 3 and further comprising:
   a lumen inside the catheter tube and extending therein from the second connector fitting to a point adjacent the end of the catheter in the endotracheal tube,
   the conduit being in fluid communication with the lumen to deliver irrigation fluid from the pump to said point adjacent the end of the catheter.

5. The apparatus of claim 1 and further comprising:
   an irrigating fluid reservoir holding irrigating fluid and fluidly connected to the pump.

6. The apparatus of claim 5 and wherein:
   the reservoir is an IV infusion bag.

7. A method of irrigating a suction catheter and comprising the steps of:
   holding a patient end fitting of a sheathed catheter tube apparatus in place adjacent a trachea entrance, with one hand;
   holding a machine coupling end of the catheter tube apparatus with the other hand;
   and pumping irrigation fluid to the catheter tube with a digit of the one hand operating the pump while holding the patient end fitting with the one hand.

8. The method of claim 7 and further comprising the steps of:
   supplying irrigating fluid to the pump from a fluid reservoir.

9. The method of claim 7 and further comprising the steps of:
   applying suction to the catheter while holding and pumping.

10. The method of claim 9 and further comprising the steps of:
    controlling the amount of suction applied by operation of a valve at the machine coupling end of the apparatus with a digit of the other hand.

* * * * *